United States Patent
Johnson et al.

(10) Patent No.: US 7,699,865 B2
(45) Date of Patent: Apr. 20, 2010

(54) ACTUATING CONSTRAINING MECHANISM

(75) Inventors: Steven W. Johnson, West Jordan, UT (US); Daryl R. Edmiston, Sandy, UT (US); Richard J. Linder, Sandy, UT (US)

(73) Assignee: Rubicon Medical, Inc., Salt Lake City, UT (US)

( * ) Notice: Subject to any disclaimer, the term of this patent is extended or adjusted under 35 U.S.C. 154(b) by 1103 days.

(21) Appl. No.: 10/936,886

(22) Filed: Sep. 9, 2004

(65) Prior Publication Data

US 2005/0085848 A1      Apr. 21, 2005

Related U.S. Application Data

(60) Provisional application No. 60/502,435, filed on Sep. 12, 2003, provisional application No. 60/503,154, filed on Sep. 15, 2003.

(51) Int. Cl.
*A61F 2/01* (2006.01)
(52) U.S. Cl. ...................... 606/200; 606/194
(58) Field of Classification Search ....... 623/1.11–1.15, 623/1.1, 1.23, 23.72; 606/191–200, 113, 606/114, 127
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,195,637 A | 4/1980 | Gruntzig et al. | 128/348 |
| 4,271,839 A | 6/1981 | Fogarty et al. | 128/344 |
| 4,307,722 A | 12/1981 | Evans | 128/344 |
| 4,323,071 A | 4/1982 | Simpson et al. | 128/343 |
| 4,367,747 A | 1/1983 | Witzel | 128/344 |
| 4,413,989 A | 11/1983 | Schjeldahl et al. | 604/96 |
| 4,425,908 A | 1/1984 | Simon | 128/1 R |
| 4,447,227 A | 5/1984 | Kotsanis | |
| 4,468,224 A | 8/1984 | Enzmann et al. | 604/247 |
| 4,540,404 A | 9/1985 | Wolvek | 604/96 |
| 4,552,554 A | 11/1985 | Gould et al. | 604/51 |
| 4,643,184 A | 2/1987 | Mobin-Uddin | |
| 4,662,885 A | 5/1987 | DiPisa, Jr. | |
| 4,705,517 A | 11/1987 | DiPisa, Jr. | |
| 4,706,671 A | 11/1987 | Weinrib | 128/348.1 |
| 4,723,549 A | 2/1988 | Wholey et al. | 128/344 |
| 4,744,366 A | 5/1988 | Jang | 128/344 |

(Continued)

FOREIGN PATENT DOCUMENTS

DE          4030998 C2     4/1991

(Continued)

*Primary Examiner*—Glenn K Dawson
*Assistant Examiner*—Kathleen Sonnett
(74) *Attorney, Agent, or Firm*—Crompton, Seager & Tufte LLC

(57) ABSTRACT

Disclosed is a constraining mechanism that enhances the strength of a medical device, while also preventing over expansion of the device, during a procedure. The medical device includes a plurality of biased struts to which a constraining mechanism is coupled. The constraining mechanism includes a spine, which couples to one of the plurality of struts, and one or more branches extending from the spine. The branches have a curvature enabling the branches to substantially surround the plurality of struts while at the same time avoiding contact with the wall of the blood vessel of the patient when the medical device is deployed.

9 Claims, 4 Drawing Sheets

U.S. PATENT DOCUMENTS

| | | | |
|---|---|---|---|
| 4,748,982 A | 6/1988 | Horzewski et al. ......... 128/344 |
| 4,762,129 A | 8/1988 | Bonzel ....................... 128/344 |
| 4,771,777 A | 9/1988 | Horzewski et al. ......... 128/344 |
| 4,790,812 A | 12/1988 | Hawkins, Jr. et al. ......... 604/22 |
| 4,790,813 A | 12/1988 | Kensey |
| 4,793,348 A | 12/1988 | Palmaz ....................... 128/325 |
| 4,794,928 A | 1/1989 | Kletschka .................... 128/344 |
| 4,857,045 A | 8/1989 | Rydell |
| 4,873,978 A | 10/1989 | Ginsburg ..................... 128/345 |
| 4,886,061 A | 12/1989 | Fischell et al. |
| 4,926,858 A | 5/1990 | Gifford, III et al. ......... 606/159 |
| 4,946,466 A | 8/1990 | Pinchuk et al. ............. 606/194 |
| 4,964,409 A | 10/1990 | Tremulis ..................... 128/657 |
| 4,969,890 A | 11/1990 | Sugita et al. ................. 606/192 |
| 4,969,891 A | 11/1990 | Gewertz |
| 4,983,167 A | 1/1991 | Sahota ........................ 606/194 |
| 5,011,488 A | 4/1991 | Ginsburg .................... 606/159 |
| 5,015,253 A * | 5/1991 | MacGregor ................ 623/1.15 |
| 5,026,377 A | 6/1991 | Burton et al. ............... 606/108 |
| 5,040,548 A | 8/1991 | Yock .......................... 128/898 |
| 5,061,267 A | 10/1991 | Zeither ....................... 606/40 |
| 5,071,407 A | 12/1991 | Termin et al. ............... 604/104 |
| 5,100,423 A | 3/1992 | Fearnot ....................... 606/159 |
| 5,102,390 A | 4/1992 | Crittenden et al. ........... 604/96 |
| 5,104,399 A | 4/1992 | Lazarus ........................ 623/1 |
| 5,108,419 A | 4/1992 | Reger et al. ................. 606/200 |
| 5,133,733 A | 7/1992 | Rasmussen et al. |
| 5,135,487 A | 8/1992 | Morrill et al. ................ 604/96 |
| 5,135,535 A | 8/1992 | Kramer ....................... 606/194 |
| 5,152,777 A | 10/1992 | Goldberg et al. ............ 606/200 |
| 5,156,594 A | 10/1992 | Keith .......................... 604/96 |
| 5,160,342 A | 11/1992 | Reger et al. ................. 606/200 |
| 5,180,367 A | 1/1993 | Kontos et al. ............... 604/101 |
| 5,192,286 A | 3/1993 | Phan et al. |
| 5,209,729 A | 5/1993 | Hofmann et al. ............. 604/96 |
| 5,209,730 A | 5/1993 | Sullivan ....................... 604/96 |
| 5,226,909 A | 7/1993 | Evans et al. ................. 606/159 |
| 5,232,445 A | 8/1993 | Bonzel ........................ 604/96 |
| 5,266,473 A | 11/1993 | Nielsen |
| 5,271,415 A | 12/1993 | Foerster et al. ............. 128/772 |
| 5,275,151 A | 1/1994 | Shocket et al. ................ 128/4 |
| 5,279,560 A | 1/1994 | Morrill et al. ................ 604/96 |
| 5,300,025 A | 4/1994 | Wantink ...................... 604/96 |
| 5,311,858 A | 5/1994 | Adair ............................ 128/4 |
| 5,315,996 A | 5/1994 | Lundquist ................... 128/642 |
| 5,320,605 A | 6/1994 | Sahota ........................ 604/101 |
| 5,324,304 A | 6/1994 | Rasmussen |
| 5,328,472 A | 7/1994 | Steinke et al. ............... 604/102 |
| 5,329,942 A | 7/1994 | Gunther et al. .............. 128/898 |
| 5,342,297 A | 8/1994 | Jang ............................ 604/53 |
| 5,364,357 A | 11/1994 | Aase ........................... 604/96 |
| 5,370,657 A | 12/1994 | Irie |
| 5,376,100 A | 12/1994 | Lefebvre ..................... 606/180 |
| 5,380,283 A | 1/1995 | Johnson ....................... 604/96 |
| 5,387,226 A | 2/1995 | Miraki ........................ 606/194 |
| 5,395,332 A | 3/1995 | Ressemann et al. ........... 604/96 |
| 5,399,165 A | 3/1995 | Paul, Jr. ....................... 604/95 |
| 5,405,378 A | 4/1995 | Strecker ........................ 623/1 |
| 5,409,458 A | 4/1995 | Khairkhahan et al. ........ 604/96 |
| 5,415,630 A | 5/1995 | Gory et al. |
| 5,419,774 A | 5/1995 | Willard et al. |
| 5,421,832 A | 6/1995 | Lefebvre ....................... 604/53 |
| 5,437,288 A | 8/1995 | Schwartz et al. ............ 128/772 |
| 5,441,483 A | 8/1995 | Avitall ......................... 604/95 |
| 5,456,694 A | 10/1995 | Marin et al. ................ 606/198 |
| 5,458,613 A | 10/1995 | Gharibadeh et al. ......... 606/194 |
| 5,462,529 A | 10/1995 | Simpson et al. |
| 5,490,837 A | 2/1996 | Blaeser et al. ................ 604/96 |
| 5,490,859 A | 2/1996 | Mische et al. ............... 606/159 |
| 5,497,785 A | 3/1996 | Viera .......................... 128/772 |
| 5,507,731 A | 4/1996 | Hernandez et al. .......... 604/264 |
| 5,536,242 A | 7/1996 | Willard et al. |
| 5,549,553 A | 8/1996 | Ressemann et al. ........... 604/96 |
| 5,549,556 A | 8/1996 | Ndondo-Lay et al. ....... 604/102 |
| 5,549,626 A | 8/1996 | Miller et al. ................ 606/200 |
| 5,578,009 A | 11/1996 | Kraus et al. .................. 604/96 |
| 5,599,492 A | 2/1997 | Engelson .................... 264/167 |
| 5,605,543 A | 2/1997 | Swanson ...................... 604/96 |
| 5,634,942 A | 6/1997 | Chevillon et al. .............. 623/1 |
| 5,662,671 A | 9/1997 | Barbut et al. |
| 5,669,932 A | 9/1997 | Fischell et al. ............. 606/198 |
| 5,669,933 A | 9/1997 | Simon et al. |
| 5,683,411 A | 11/1997 | Kavteladze et al. |
| 5,695,519 A | 12/1997 | Summers et al. ............ 606/200 |
| 5,707,359 A | 1/1998 | Bufalini ...................... 606/200 |
| 5,709,704 A | 1/1998 | Nott et al. ................... 606/200 |
| 5,720,764 A | 2/1998 | Naderlinger ................ 606/200 |
| 5,735,859 A * | 4/1998 | Fischell et al. .............. 606/108 |
| 5,769,816 A | 6/1998 | Barbut et al. ................. 604/96 |
| 5,769,858 A | 6/1998 | Pearson et al. .............. 606/108 |
| 5,779,716 A | 7/1998 | Cano et al. |
| 5,782,809 A | 7/1998 | Umeno et al. ............... 604/280 |
| 5,792,300 A | 8/1998 | Inderbitzen et al. |
| 5,795,322 A | 8/1998 | Boudewijn .................... 604/22 |
| 5,800,457 A | 9/1998 | Gelbfish ..................... 606/200 |
| 5,800,525 A | 9/1998 | Bachinski et al. |
| 5,807,330 A | 9/1998 | Teitelbaum .................. 604/96 |
| 5,807,398 A | 9/1998 | Shaknovich |
| 5,810,874 A | 9/1998 | Lefebvre .................... 606/200 |
| 5,814,064 A | 9/1998 | Daniel et al. ................ 606/200 |
| 5,817,104 A | 10/1998 | Bilitz et al. ................. 606/127 |
| 5,827,324 A | 10/1998 | Cassell et al. ............... 606/200 |
| 5,833,632 A | 11/1998 | Jacobsen et al. ............. 600/585 |
| 5,833,650 A | 11/1998 | Imran |
| 5,836,969 A | 11/1998 | Kim et al. ................... 606/200 |
| 5,843,050 A | 12/1998 | Jones et al. ................. 604/280 |
| 5,848,964 A | 12/1998 | Samuels |
| 5,873,906 A | 2/1999 | Lau et al. ........................ 623/1 |
| 5,876,367 A | 3/1999 | Kaganov et al. ............... 604/8 |
| 5,895,399 A | 4/1999 | Barbut et al. ................ 606/159 |
| 5,910,154 A | 6/1999 | Tsugita et al. ............... 606/200 |
| 5,911,734 A | 6/1999 | Tsugita et al. ............... 606/200 |
| 5,919,225 A | 7/1999 | Lau et al. .................... 606/198 |
| 5,921,924 A | 7/1999 | Avitall ........................ 600/374 |
| 5,954,745 A | 9/1999 | Gertler et al. ............... 606/200 |
| 6,001,118 A | 12/1999 | Daniel et al. ................ 606/200 |
| 6,004,279 A | 12/1999 | Crowley et al. ............. 600/585 |
| 6,007,558 A | 12/1999 | Ravenscroft et al. ........ 606/200 |
| 6,022,336 A | 2/2000 | Zadno-Azizi et al. ......... 604/96 |
| 6,036,717 A | 3/2000 | Mers Kelly et al. ......... 606/200 |
| 6,042,598 A | 3/2000 | Tsugita et al. ............... 606/200 |
| 6,048,338 A | 4/2000 | Larson et al. ................ 604/523 |
| 6,053,932 A | 4/2000 | Daniel et al. ................ 606/200 |
| 6,059,814 A | 5/2000 | Ladd .......................... 606/200 |
| 6,066,149 A | 5/2000 | Samson et al. |
| 6,066,158 A | 5/2000 | Engelson et al. |
| 6,099,549 A | 8/2000 | Bosma et al. ............... 606/200 |
| 6,110,170 A | 8/2000 | Taylor et al. .................. 606/49 |
| 6,126,685 A | 10/2000 | Lenker et al. ............... 606/194 |
| 6,129,739 A | 10/2000 | Khosravi |
| 6,142,987 A | 11/2000 | Tsugita |
| 6,146,396 A | 11/2000 | Kónya et al. ................ 606/159 |
| 6,152,946 A | 11/2000 | Broome et al. .............. 606/200 |
| 6,165,200 A | 12/2000 | Tsugita et al. ............... 606/200 |
| 6,168,579 B1 | 1/2001 | Tsugita |
| 6,168,603 B1 | 1/2001 | Leslie et al. ................. 606/200 |
| 6,168,604 B1 | 1/2001 | Cano .......................... 606/114 |
| 6,168,616 B1 * | 1/2001 | Brown, III .................. 623/1.11 |
| 6,171,327 B1 | 1/2001 | Daniel et al. ................ 606/200 |
| 6,171,328 B1 | 1/2001 | Addis ......................... 606/200 |
| 6,174,318 B1 | 1/2001 | Bates et al. ................. 606/200 |
| 6,178,968 B1 | 1/2001 | Louw et al. ................. 128/898 |
| 6,179,859 B1 | 1/2001 | Bates et al. ................. 606/200 |
| 6,179,860 B1 | 1/2001 | Fulton, III et al. .......... 606/200 |

| | | |
|---|---|---|
| 6,179,861 B1 | 1/2001 | Khosravi et al. |
| 6,203,561 B1 | 3/2001 | Ramee et al. |
| 6,206,868 B1 | 3/2001 | Parodi |
| 6,217,567 B1 | 4/2001 | Zadno-Azizi et al. ........ 604/530 |
| 6,221,006 B1 | 4/2001 | Dubrul et al. |
| 6,241,746 B1 * | 6/2001 | Bosma et al. .............. 606/200 |
| 6,245,087 B1 | 6/2001 | Addis ......................... 606/200 |
| 6,245,089 B1 | 6/2001 | Daniel et al. ................ 606/200 |
| 6,254,628 B1 | 7/2001 | Wallace et al. ............ 623/1.12 |
| 6,277,139 B1 | 8/2001 | Levinson et al. ............ 606/200 |
| 6,290,710 B1 | 9/2001 | Cryer et al. ................. 606/200 |
| 6,344,049 B1 | 2/2002 | Levinson et al. |
| 6,352,561 B1 * | 3/2002 | Leopold et al. ............ 623/1.23 |
| 6,355,051 B1 | 3/2002 | Sisskind et al. ............. 606/200 |
| 6,361,545 B1 | 3/2002 | Macoviak et al. ........... 606/200 |
| 6,383,206 B1 | 5/2002 | Gillick et al. ............... 606/200 |
| 6,423,086 B1 | 7/2002 | Barbut et al. ............... 606/200 |
| 6,447,540 B1 | 9/2002 | Fontaine et al. ............ 623/1.12 |
| 6,468,298 B1 | 10/2002 | Pelton ....................... 623/1.11 |
| 6,485,501 B1 | 11/2002 | Green ........................ 606/200 |
| 6,511,503 B1 | 1/2003 | Burkett et al. |
| 6,537,294 B1 | 3/2003 | Boyle et al. |
| 6,537,295 B2 | 3/2003 | Petersen .................... 606/200 |
| 6,558,396 B1 | 5/2003 | Inoue ........................ 606/108 |
| 6,562,058 B2 | 5/2003 | Seguin et al. ............... 606/200 |
| 6,605,102 B1 | 8/2003 | Mazzocchi et al. |
| 6,623,450 B1 | 9/2003 | Dutta |
| 6,656,213 B2 | 12/2003 | Solem ........................ 623/1.11 |
| 6,702,845 B1 | 3/2004 | Cully et al. |
| 6,743,219 B1 | 6/2004 | Dwyer et al. ............... 604/525 |
| 6,814,746 B2 | 11/2004 | Thompson et al. |
| 6,964,670 B1 | 11/2005 | Shah et al. |
| 2001/0031981 A1 | 10/2001 | Evans et al. ................ 606/200 |
| 2002/0016564 A1 | 2/2002 | Courtney et al. ......... 604/96.01 |
| 2002/0029077 A1 | 3/2002 | Leopold et al. ............ 623/1.11 |
| 2002/0055767 A1 | 5/2002 | Forde et al. ................ 623/1.11 |
| 2002/0193824 A1 | 12/2002 | Boylan et al. |
| 2003/0032941 A1 | 2/2003 | Boyle et al. |
| 2003/0065354 A1 | 4/2003 | Boyle et al. |
| 2003/0199920 A1 | 10/2003 | Boylan et al. |
| 2003/0212410 A1 | 11/2003 | Stenzel et al. ............... 606/108 |
| 2004/0006361 A1 | 1/2004 | Boyle et al. |
| 2004/0049204 A1 | 3/2004 | Harari et al. |
| 2004/0087900 A1 | 5/2004 | Thompson et al. |
| 2004/0087965 A1 | 5/2004 | Levine et al. ............... 606/108 |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0158281 A1 | 8/2004 | Boylan et al. |
| 2004/0167568 A1 | 8/2004 | Boyle et al. |
| 2004/0172055 A1 | 9/2004 | Huter et al. |
| 2004/0260331 A1 | 12/2004 | D'Aquanni et al. |
| 2004/0267301 A1 | 12/2004 | Boylan et al. |
| 2005/0004595 A1 | 1/2005 | Boyle et al. |
| 2005/0075663 A1 | 4/2005 | Boyle et al. |
| 2005/0137677 A1 | 6/2005 | Rush |
| 2005/0209672 A1 | 9/2005 | George et al. |

FOREIGN PATENT DOCUMENTS

| | | |
|---|---|---|
| EP | 0564894 B1 | 10/1993 |
| EP | 0737450 A1 | 10/1996 |
| EP | 0737450 B1 | 11/2003 |
| GB | 2 020 557 A | 5/1979 |
| WO | 96/01591 A1 | 1/1996 |
| WO | WO 96/01591 | 1/1996 |
| WO | WO 98/02084 | 1/1998 |
| WO | WO 98/02112 | 1/1998 |
| WO | WO 98/33443 | 6/1998 |
| WO | WO 00/20064 | 4/2000 |
| WO | WO 01/91844 | 12/2001 |

* cited by examiner

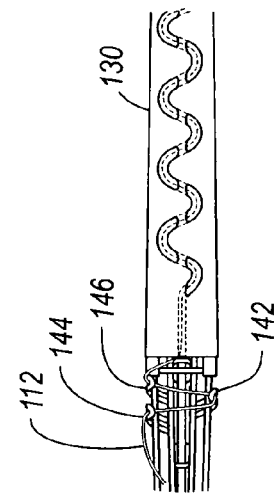
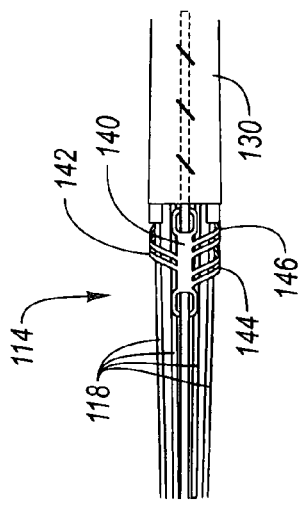
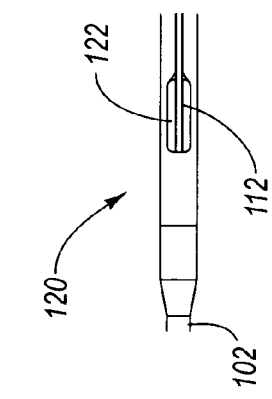
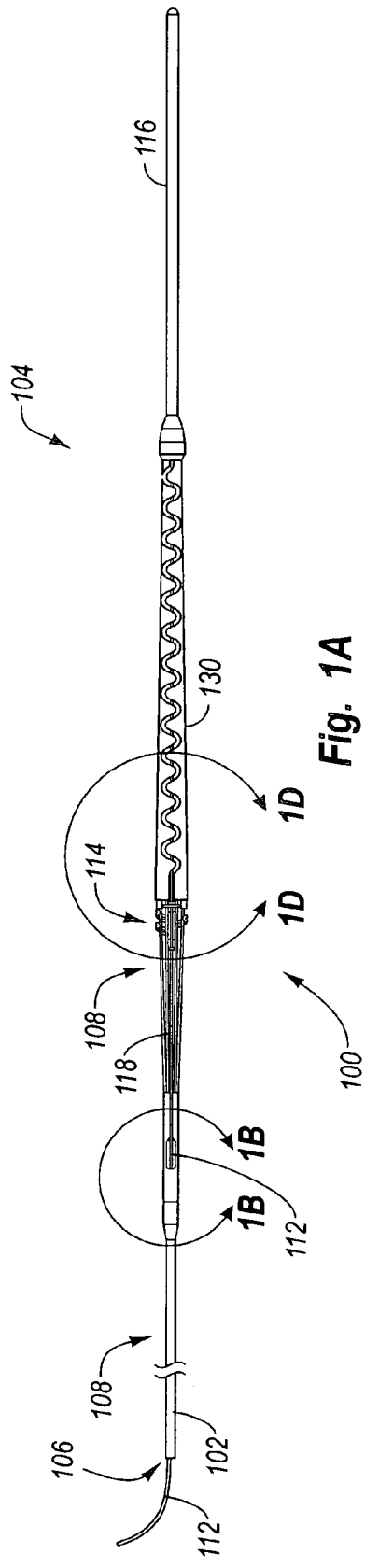

ACTUATING CONSTRAINING MECHANISM

CROSS-REFERENCE TO RELATED APPLICATIONS

This patent application claims priority to and the benefit of U.S. Provisional Patent Application Ser. No. 60/502,435, filed on Sep. 12, 2003 and entitled "Methods, Systems and Devices for Providing Embolic Protection and Removing Embolic Material"; and U.S. Provisional Patent Application Ser. No. 60/503,154, filed on Sep. 15, 2003 and entitled "Methods, Systems and Devices for Providing Embolic Protection and Removing Embolic Material", both of which are hereby incorporated by reference in their entireties.

This application also relates to U.S. patent application Ser. No. 10/936,857, now U.S. Patent Publication No. 2005/0096692, filed Sep. 9, 2004, and entitled "Methods, Systems, And Devices for Providing Embolic Protection and Removing Embolic Material", U.S. patent application Ser. No. 10/186,275, filed Jun. 28, 2002, and entitled "Methods, System, And Devices for Providing Embolic Protection and Removing Embolic Material,", now U.S. Pat. No. 6,878,153, and U.S. patent application Ser. No. 10/290,099, filed Nov. 7, 2002, and entitled "Methods, Systems, and Devices for Delivering Stents," now U.S. Pat. No. 7,594,926, which applications are incorporated herein by reference.

BACKGROUND OF THE INVENTION

1. The Field of the Invention

The invention generally relates to interventional cardiology. More specifically, the invention relates to procedures performed within a body lumen. The invention further relates to systems for providing embolic protection during procedures performed in a body lumen.

2. The Relevant Technology

Human blood vessels often become blocked with deposits such as plaque, thrombi, and other materials. If the blockage occurs at a critical place in the vessel, serious and permanent injury, or even death, can occur. To prevent these results, medical intervention is performed to clear the occluded vessel.

Several procedures are currently used to open stenosed or occluded blood vessels. Balloon angioplasty is a well known method for opening occluded blood vessels which involves inserting a balloon-tipped catheter into an occluded region of a blood vessel. After being inserted into the blood vessel, the balloon is inflated and the stenosed region of the blood vessel is dilated, thereby increasing the intraluminal diameter.

Another technique for opening stenosed blood vessels is atherectomy. Atherectomy refers to a procedure which employs a rotating blade to shave plaque from an arterial wall. A catheter including a rotating blade or cutter is inserted into the blood vessel. Located at the tip of the catheter is an aperture and, on the opposite side of the catheter tip from the aperture, a balloon. The tip is placed in close proximity to the fatty material and the balloon is inflated, thereby forcing the aperture into contact with the fatty material. When the blade or cutter is rotated, the fatty material is shaved off and retained within the interior lumen of the catheter. This process is then repeated until sufficient fatty material has been removed from the wall of the blood vessel.

An additional procedure for opening stenosed or occluded blood vessels includes stent introduction. A stent typically includes a cylindrical tube or mesh sleeve made from materials such as NiTiNOL or stainless steel. The characteristics of the material permit the diameter of the device to expand radially while still providing sufficient rigidity such that the stent maintains its shape once it has been enlarged to the desired size.

Many medical devices are used in placing a stent in a body lumen. After access to the arterial system has been established, a guide catheter is inserted into the artery and the tip of the catheter is positioned proximal to the occluded region of the blood vessel. A guide catheter allows other devices to be rapidly delivered to the stenosed region without being carefully guided from the point of access to the arterial system to the point of intervention. A small diameter guide wire is inserted through the catheter and guided to a point proximate the stenosed region. After the guidewire has been successfully put in place, the stent is attached to a delivery device and installed over the guide wire. When correctly placed, the stent will be deployed in a manner which will maintain the blood vessel open at that point.

Many different types of stents are used in intravenous procedures. Often a system requires a stent to be deployed or expanded from a compressed state by a balloon to which the stent is attached. When the balloon is inflated not only is the stenosed region opened, the stent is also embedded into the inner region of the blood vessel at that point.

The guidewire not only facilitates delivery of the stent to the stenosed region, it also serves the purpose of providing a delivery mechanism for all other devices which may be used in the procedure. Devices which may be needed in the procedure contain an inner lumen through which the guidewire is inserted. The device then slides along the guidewire into the body of the patient, with the guidewire guiding the device to the desired location. The process of sliding devices over the guidewire for delivery into the patient is commonly known as an exchange. The ability to perform an exchange reduces the invasive nature of the interventional procedure.

When interventional procedures are performed with occluded blood vessels, particles are released from the vessel wall. These embolic pieces can then flow downstream potentially causing adverse effects. To prevent the dangers associated with embolic particles flowing through the blood stream, devices are emerging which are designed to catch or filter such particles. The particles are then aspirated out of the blood stream before they can flow downstream.

Filter and trapping systems designed to capture particulate matter released during intravenous procedures include many forms. Trapping devices are often structured as an umbrella-like device designed to catch emboli as they are released from the vessel wall during an atherectomy or angioplasty procedure. Filter devices are also designed to catch released embolic material and can be either permanently or temporarily deployed in the blood vessel.

Both permanent and temporary filtering devices can present serious difficulties. Accurate deployment of permanent filtering devices is difficult and incorrect placement can limit filtering capabilities. Furthermore, permanent devices have been designed to filter large blood clots and have proven ineffective for trapping smaller emboli. In certain cases a permanent filter may accumulate too much clot and block of the area of the blood vessel in which it rests. In addition, permanent filters are often secured to the vessel wall by anchoring hooks which, with time, may cause the vessel wall to rupture due to erosion. Temporary filters, while circumventing many of the problems present in permanent devices, also present certain difficulties. Even if temporary filters succeed in capturing emboli from within the blood vessel it is difficult to remove the filter without redepositing the emboli into the blood stream.

The device and methods described herein are designed to overcome these and other deficiencies in current devices and to allow safer and better protection for the patient from particulates which may be released into the blood stream during an intravenous procedure.

BRIEF SUMMARY OF THE INVENTION

Embodiments of the present invention include filter devices that have small or low profiles, few parts and components, and are simple to manufacture and use. Consequently, embodiments of the present invention are able to be easily inserted into a patient, be steerable through the tortuous anatomy of a patient, provide filtering capabilities, have a sufficiently low profile to provide exchange capability so other medical devices can be advanced along the filter device, and be capable of removing the captured material without allowing such material to escape during filter retrieval.

According to one embodiment of the present invention, the filter device can include a guide member having a lumen extending from a distal end to a proximal end of the guide member. The distal end can include a tip to aid in guiding the device through a blood vessel of a patient. The proximal end extends from the body of the patient and can be engaged by a physician or other medical technician. Disposed within the lumen near the distal end of the filter device are the filter assembly and one or more actuating members. The one or more actuating members are coupled to an actuating mechanism at the proximal end of the guide member and are configured to deploy the filter assembly during a procedure, such as through movement of one or more actuating members.

The filter assembly can include a filter and a plurality of radially spaced biased struts attached to the distal end of the filter assembly. The struts expand outwardly upon being deployed from the lumen of the guide member to place the peripheral edge of the distal end of the filter adjacent the wall of the vessel.

The filter includes a plurality of pores or holes that are sized so as to capture material that may become detached during the procedure. The filter is configured to be constrained against the blood vessel within which the filter is disposed, and then open to collect material and maintain the flow of blood through the vessel. The distal end of the filter can optionally change shape to collect the emboli.

In one embodiment the filter assembly can include a constraining mechanism to prevent the filter assembly from opening or extending outwardly before it is deployed within the blood vessel of the patient. The constraining mechanism can perform the function of restraining one or more expandable portions of the medical device.

In one embodiment a constraining mechanism substantially surrounds a proximal portion of the struts of the filter assembly, while a sleeve applies a constraining or restraining force to the remainder of the struts. The sleeve can attach at some distal portion of the filter device while having the other end of the sleeve attached to a portion of the filter device, such as at one or more struts or at or near the proximal end of the filter assembly. An actuating member can be attached to a portion of the proximal end of the sleeve to selectively maintain the sleeve about the struts. The actuating member can be moved in such a way as to open the sleeve, thus allowing the struts to move outwardly and deploy the filter within the blood vessel.

In one embodiment the constraining mechanism can cooperate with the sleeve to limit the movement of the expandable portion of the medical device. The constraining mechanism can include a spine that cooperates with one of the struts and branches that can extend from the spine and at least partially surround the expanding struts and apply a restraining force upon the struts. The branches of the constraining mechanism can include and engagement means for receiving the actuating member. The branches can also be biased, allowing the branches to maintain their restraining force as the actuating mechanism is engaged with the branches. When the actuating member is disengaged, the branches move away from the struts and the struts can move outwardly to deploy the filter. The actuating member can be disengaged when a physician or other medical technician engages the actuating mechanism located at the proximal end of the filter device.

The constraining mechanism of the filter assembly can be manufactured from a substantially planar sheet of material. The sheet of material can be inspected at various regions of the sheet to ensure a uniformity of thickness of the sheet, thus ensuring a uniformity of the thickness of the constraining mechanisms themselves. The design of the constraining mechanisms is then implanted on the sheet using a process such as an etching process. Due to the difference between the size of the relatively small constraining mechanism and the relatively large sheet of material, numerous constraining mechanisms can be manufactured from a single sheet of material. Once the design of the constraining mechanism is formed on the sheet the excess material is removed. The constraining mechanisms can then be further formed into curved shape using a process such as heat setting.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 1A-1D illustrates one embodiment of a medical device in a constrained position, showing the guide member, filter device, and constraining mechanism;

DETAILED DESCRIPTION OF THE EXEMPLARY EMBODIMENTS

Figure 2:
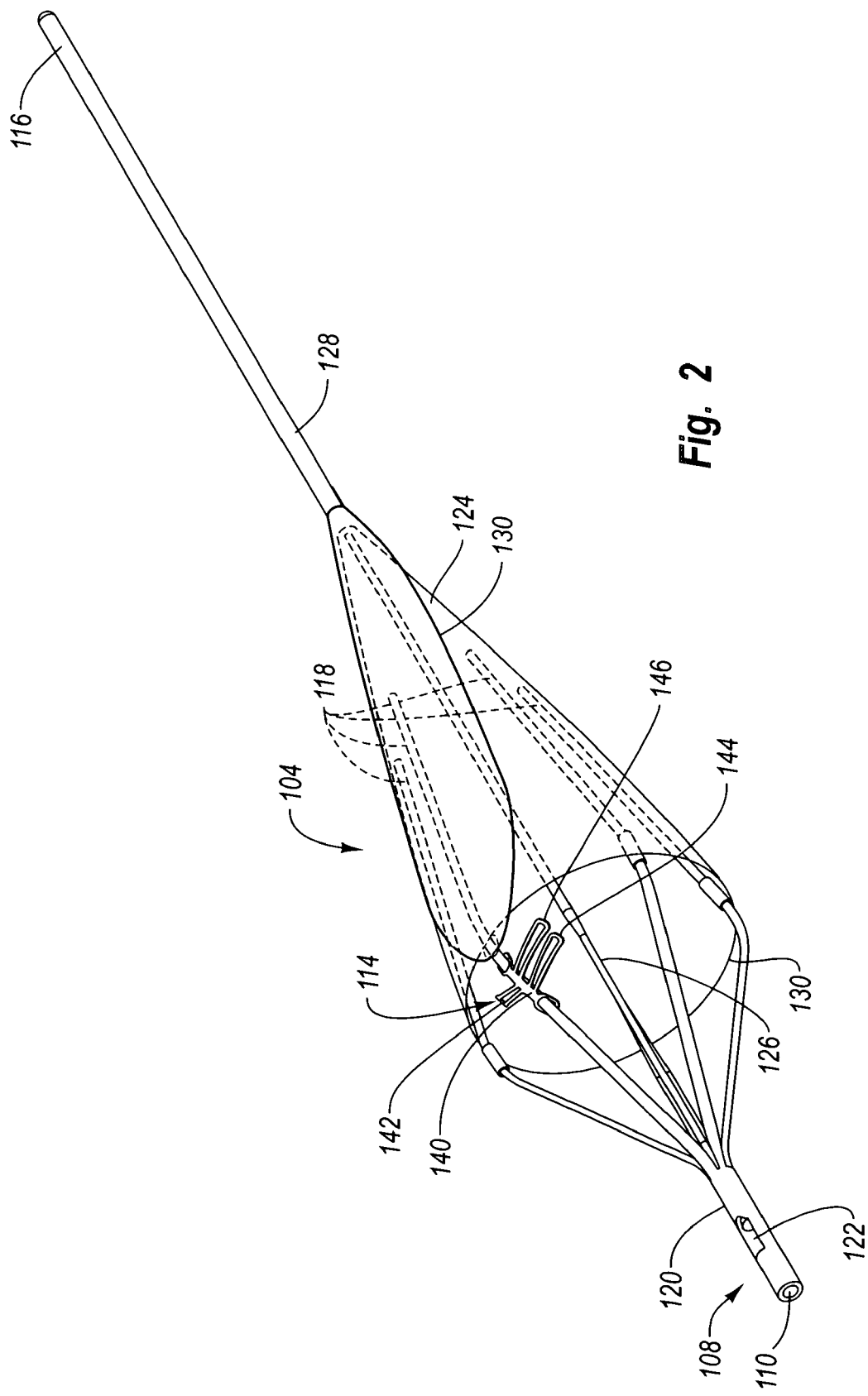
FIG. 2 illustrates one embodiment of the medical device of FIG. 1 in a deployed position.

The present invention generally relates to techniques and devices for restraining at least a portion of an expandable medical device. Discussion will be made herein to use of the invention with percutaneous filter devices, systems, and methods of using the same. Although reference is made to such devices, systems, and methods, one skilled in the art will understand that various medical devices or other devices may benefit from utilizing the present invention.

The present invention is generally a constraining mechanism that can be used to limit movement of an expandable portion of a medical device. For instance, when the medical devices is a percutaneous filter having one or more biased struts, the constraining mechanism can be configured with branches that are curved in such a way as to substantially surround struts of the filter device and operate to prevent expansion of the struts until the physician or medical technician deactivates the constraining mechanism. Optionally, the constraining mechanism can prevent unwanted contact between the constraining mechanism, the struts, and the wall of the blood vessel. This constraining mechanism can constrain movement of the struts alone or in cooperation with one or more other restraining mechanisms.

Referring now to FIG. 1A showing a constrained view of the medical device, depicted is one exemplary embodiment of the medical device of the present invention, identified by reference numeral 100. As illustrated, medical device 100 includes a guide member 102 with a filter device 104 mounted thereto. The guide member 102 can have a proximal end 106 that remains outside of the patient during a procedure and a distal end 108 that can be disposed within a patient's body lumen. As shown, distal end 108 of guide member 102 can receive filter device 104. The filter device 104 cooperates with a lumen (not shown) that extends from distal end 108 toward proximal end 106 to receive a portion of an actuating member 112, as shown in FIG. 1B; this actuating member 112 can aid in selectively releasing and constraining filter device 104 as it cooperates with a constraining mechanism 114 and/or a sleeve 130 shown in FIGS. 1C and 1D.

The medical device 100 can meet criteria for both guidewires and filter devices. For instance, it is desirable that a guidewire is steerable. Consequently, medical device 100 can be insertable within any blood vessel of a patient, such as but not limited to, coronary artery, carotid arteries, renal arteries, bypass grafts, superficial femoral artery, the arteries of the upper and lower extremities, or cerebral vasculature, and, with the help of a shapeable, soft, distal tip 116 mounted to or forming part of filter device 104, manipulated and steered by a physician to traverse the tortuous anatomy of the patient to a lesion or occlusion.

Further, medical device 100, including guide member 102, can translate rotational movement or force applied to proximal end 106 thereof substantially equally to distal end 108 and so to filter device 104. In other words, with the filter device positioned within a vessel of the patient, as a physician rotates the proximal end of the filter device, the distal end of the filter device rotates substantially simultaneously with the movement of the proximal end. This is typically defined as having a one-to-one torqueability.

The medical device 100, including guide member 102, can be kink resistant and can receive a variety of different coatings to improve lubricity, have anti-thrombogenic properties, and/or reduce platelet aggregation. These coatings can include, but are not limited to, a hydrophilic coating, a heparinized coating, Teflon, silicone, or other coating known to those skilled in the art in light of the teaching contained herein.

With reference now to FIG. 2, showing medical device 100 in a deployed configuration, mounted to guide member 102 is filter device 104. The filter device 104 can include a plurality of struts 118 that are biased to extend outwardly. The struts 118 extend from a base portion 120 that connects to guide member 102. This base portion 120 includes a hole 110 to receive guide member 102 and a hole (not shown) to receive a tip 116 that extends through a distal end of filter device 104. Additionally, as shown in both FIGS. 1B and 2, base portion 120 includes a hole 122 through which pass at least a portion of actuating member 112. In this manner, actuating member 112 passes through lumen 110 and through hole 122 to cooperate with constraining mechanism 114 and optionally sleeve 130, as shown in FIGS. 1A-1D.

With continued reference to FIG. 2, struts 118 can be at least partially constructed of a shape memory material. Shape memory materials are well known in the art for their ability to enable devices to assume one or more shapes depending on specific physical parameters to which the shape memory material may be exposed. A device constructed of one or more shape memory materials can be configured to transition from an initial shape to a secondary shape when the shape memory material is exposed to a known triggering condition. Examples of triggering conditions include specific predetermined temperatures, a specified pH, and other environmental conditions.

Shape memory materials suitable for use in fabrication of struts 118 include, but are not limited to, shape memory polymers, shape memory metals, such as NiTiNOL, and other materials both natural and synthetic. Several shape memory polymer materials may be suitable for fabrication of struts 118. These materials include but are not limited to: polyurethane; polycycloocetene; cross-linked polyethylene; thermoplastics such as shape memory polyurethanes, polyethylene, polynorborene polymers and copolymers and blends thereof with styrene elastomer copolymers, such as Kraton, and cross-linked transpolyoctylene rubber; cross-linked polyisoprene; styrene butadiene copolymers; bioabsorbable shape memory polymers such as polycaprolactone, copolymers, and/or PLLA PGA copolymers; PMMA; Azo-dyes, Zwitterionic and other photo chromatic materials. In addition to being well suited for fabrication of struts 118, these shape memory materials are also preferably at least partially employed in construction of tip 116 and constraining mechanism 114.

Attached to at least one of plurality of struts 118 is a filter member 124 configured to capture material of a variety of sizes and enable removal of the captured material. This filter member 124 has a plurality of pores or holes (not shown) through which a fluid can pass, while the size and shape of each pore or hole is selected to prevent passage of emboli or other material. Therefore, filter pore sizes and shapes can be selected based upon the size of material to be captured. The material can include, but is not limited to, particulates, thrombi, any atherosclerosis or plaque material dislodged during procedure, or other foreign material that may be introduced in to the vasculature of the patient.

In addition to the pores or holes preventing passage of emboli or other material, one or more of the pores or holes receive a portion of tip 116, such as an atraumatic tip. Tip 116 can include a core member 126 that extends from the hole (not shown) in base portion 120 through filter member 124. This core member 126 can be surrounded by a coil 128 that provides flexibility and radiopaque properties to tip 116 and can secure tip 116 to filter member 124 as it surrounds a portion of filter member 124. Optionally, a securing coil can surround a portion of coil 128 and the distal end of filter member 124.

Although this is one manner to connect filter member 124 to tip 116, one skilled in the art can identify various other manners to connect filter member 124 to tip 116. For instance, the distal end of filter member 124 can be bonded to tip 116 using adhesives, mechanical fasteners, crimping, seals, friction fit, press fit, or other manners to connect filter member 124 to tip 116. In another configuration, filter member 124 is not connected to tip 116 but can slide along a portion of tip 116.

As mentioned above, before deploying filter device 104 to capture emboli struts 118 are prevented from opening or extending outwardly. This constraining can be achieved through use of constraining mechanism 114 and sleeve 130. Therefore, constraining mechanism 114 and sleeve 130, either collectively or individually, can perform the function of restraining one or more expandable portions of the medical device.

With reference to FIG. 1A, constraining mechanism 114 provides a constraining or restraining force about a proximal portion of struts 118, while sleeve applies a constraining or restraining force to the remainder of struts 118. Optionally, sleeve 130 can provide a restraining force about substantially the length of the expandable portion of medical device 100.

The sleeve 130 functions as a restraining mechanism to selectively limit movement of struts 118. The sleeve 130 can attach at one end to tip 116 or some distal portion of filter device 104. The other end of sleeve 130 can attach to (i) one or more of struts 118, (ii) to a proximal end of filter device 104, (iii) or a portion of guide member 102. The sleeve 130 can surround struts 118 and can have its ends stitched together by way of actuating member 112. Stated another way, actuating member 112 can be woven or stitched through portions of sleeve 130 to selectively maintain sleeve 130 about struts 118. Removing actuating member 112 or moving actuating member 112 in a proximal direction, can unstitch sleeve 130 and enable struts 118 to move outwardly to deploy filter member 124 within the patient's body lumen. Although actuating member 112 can unstitch sleeve 130 to enable struts 118 to move outwardly, sleeve 130 can remain attached to medical device 100 to enable sleeve 130 to be removed from the patient's body lumen following the procedure.

Sleeve 130 can be formed from a variety of different materials, so long as the material is sufficiently strong to restrain one or more struts 118. For example, sleeve 130 can be fabricated from various types of polymer or silicone films, such as but not limited to, heat shrink plastic, polymer, low-density polyethylene (LDPE), polyethylene terphthalate (PET), Polytetrafluoroethylene (PTFE), fluorinated ethylene propylene (FEP), polyethylene (PE), polyurethane (PU), or silicone tubing.

Cooperating with sleeve 130 to limit movement of the expandable portion of medical device 100, in one configuration is constraining mechanism 114, as shown again in FIG. 1C. The constraining mechanism 114 can include a spine 140 that cooperates with one of struts 118 and branches 142, 144, and 146 that extend from spine 140 and at least partially surround struts 118. The spine 140 functions to limit movement of constraining mechanism 114 as branches 142, 144, and 146 at least partially surround struts 118 and apply the restraining force upon struts 118, as shown in FIG. 1C. With branches 142, 144, and 146 being biased, the restraining force applied by branches 142, 144, and 146 is maintained as actuating member 112 engages with branches 142, 144, and 146 in an alternating fashion, as shown. Upon disengaging actuating member 112, as shown in FIG. 2, branches 142, 144, and 146 move away from struts 118 and struts 118 can move outwardly to deploy filter member 124.

Figure 3:
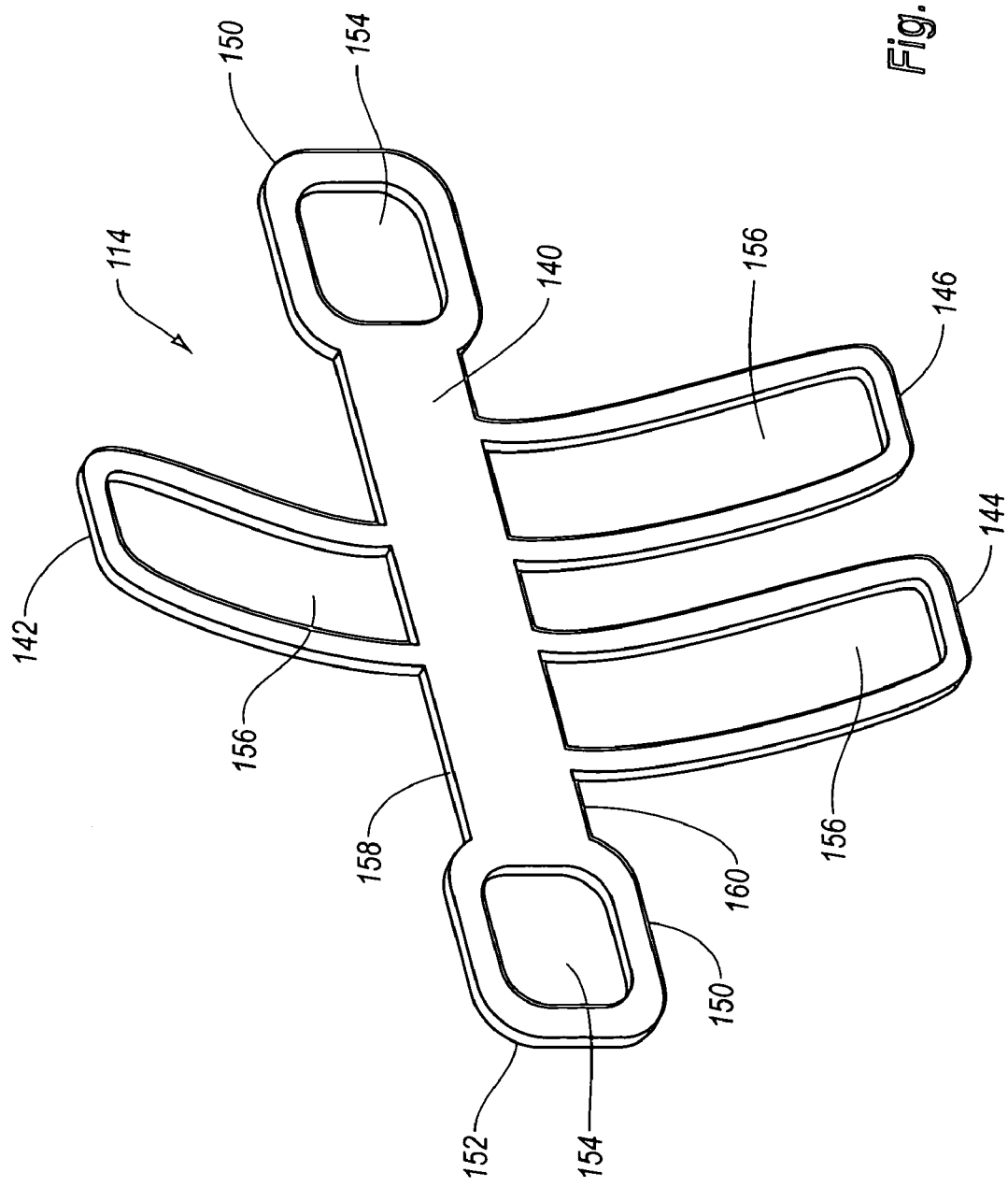
FIG. 3 illustrates a perspective view of one embodiment of the constraining mechanism of the medical device of FIG. 1.

Referring now to FIG. 3, depicted is one exemplary configuration of constraining mechanism 114 separated from filter device 104. As shown, spine 140 includes two ends 150 and 152 with holes or hollow portions 154. The hollow portions 154 of ends 150 and 152 enable spine 140 to be coupled with one of struts 118 (FIG. 2) of filter device 104 (FIG. 2). The strut 118 (FIG. 2) can be inserted through each of hollow portions 154, thus providing a secure coupling while at the same time employing a design that is simple to manufacture.

Branches 142, 144, and 146 extend from spine 140, with each branch 142, 144, and 146 having a hollow portion 156.

In one embodiment one branch 142 extends from a first side 158 of spine 140 while two branches 144 and 146 extend from a second side 160 of spine 140. In this configuration, branch 142 can extend into the gap between branches 144 and 146 upon branches 142, 144, and 146 surround struts 118. The branches 142, 144, and 146 can extend either perpendicularly to spine 140 or at some angular orientation relative to spine 140. For instance, branches 142, 144, and 146 can extend in a curved fashion from spine 140 and curve toward a distal end of filter device 104 and/or away from the walls of a patient's body lumen. By so doing, the curvature of branches 142, 144, and 146 prevents damage to the patient's body lumen during deployment and also removal of medical device 100.

Various other configurations of constraining mechanism 114 are possible. For instance, constraining mechanism 114 can include two or more branches and one or more hollow portions. In addition, various other placements of branches 142, 144, and 146 on spine 140 are possible and may be desirable for particular applications. Further, constraining mechanism 114 can be fabricated from various materials, such as but not limited to shape memory materials, like but not limited to NiTiNOL, spring metals, metals, alloys, composites, plastics, combinations thereof, or other materials as discussed supra in conjunction with fabrication of struts 118.

The medical device having a constraining mechanism of the present invention is able to capture plaque, thrombi, and various other particulates which may be released into the blood stream of the patient during a vascular procedure. This protective function is further enhanced by the constraining mechanism, which not only increases the strength of the filter device, but by its curved design also prevents any damage to the blood vessel wall when the device is inserted into the blood vessel of a patient.

Figure 4:
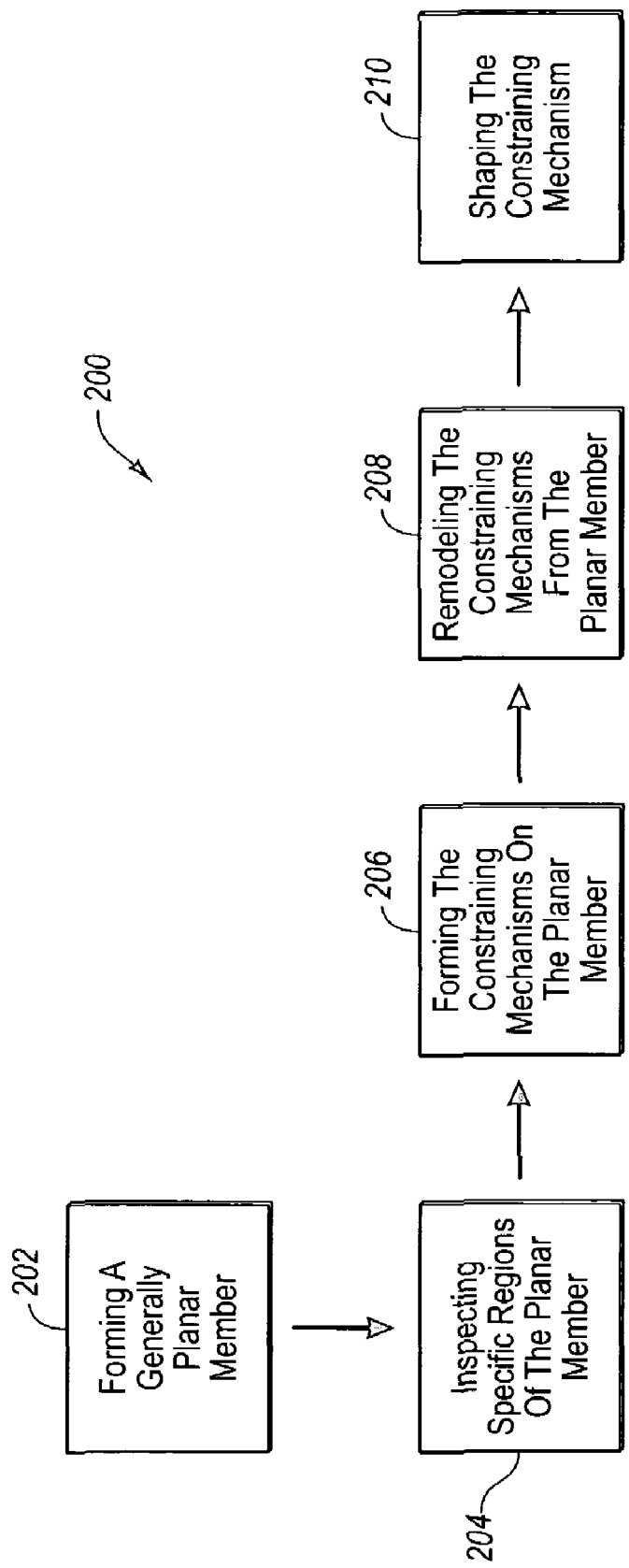
FIG. 4 is a flow diagram outlining the various steps in the manufacture of the constraining mechanism of FIG. 3.

The constraining mechanism is manufactured through a multi-step process, an example of which is schematically represented in FIG. 4 and identified by reference numeral 200. The manufacturing process 200 assures the integrity of each constraining mechanism produced, while at the same time providing an efficient means for rapidly producing numerous parts at once. The manufacturing process can involve forming a generally planar member, preferably a sheet of appropriate material of a specified thickness, from which the constraining mechanisms will be extracted, as represented by block 202. Appropriate materials for construction of the planar sheet include but are not limited to shape memory materials such as those discussed supra in connection with construction of struts 118 (FIG. 2). The particular technique for forming the planar member can include, but not limited to, photo-lithography or other chemical etching processes, die-cutting or laser-cutting.

To ensure consistency among various mechanisms to be constructed from the sheet of material, the thickness of the sheet is determined at various inspection points in various inspection regions on the sheet, as represented by block 204. This can include physical measurement by caliper, micrometer or other direct measurement devices or by indirect measurements such as optical comparison. After consistent thicknesses at the various inspection points have been verified, the constraining mechanism can be formed on the planar member, as represented by block 206. In one configuration, the constraining mechanism can be outlined on the sheet using an image implanting process, such as an etching technique, photolithography, or laser ablation. Due to the relatively small size of each constraining mechanism compared to the relatively large size of the sheet of material numerous constraining mechanisms can be manufactured using a single sheet of material.

Once the image implanting process has been completed, the constraining mechanisms can be removed from the sheet of material, as represented by block 208. This can be achieved by simply applying a sufficient force upon each constraining mechanism to break the bond between the constraining mechanism and the remainder of the sheet at the etched location.

After being removed from the sheet of material the constraining mechanism can be shaped to a desired configuration, as represented by block 210. In one embodiment where the sheet of material is constructed of a shape memory material the constraining mechanism can be heat set to a desired curvature with the appropriate radius of curvature. In another configuration, chemical etching or mechanical abrasion can modify the tension in one side of the file causing curvature. In yet another configuration, the curvature may be imparted to the material by rolling it through an appropriately configured system of tensioned rollers. When the manufacturing steps have been completed, the constraining mechanism can then be coupled to the medical device in a desired manner.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical device comprising:
    a guide member having a distal end and a proximal end;
    an expandable filter including a filter member having a plurality of pores coupled to said guide member, said expandable filter including a plurality of biased struts; and
    a mechanism mounted to at least one of said plurality of biased struts, said mechanism being adapted to limit movement of said plurality of biased struts and at least partially surround said plurality of biased struts,
    wherein said mechanism comprises a spine and one or more branches extending from said spine, said one or more branches being configured to have a curvature toward said expandable filter and at least partially surround at least a portion of said plurality of biased struts,
    wherein said spine comprises one or more ends, each of said one or more ends including a hole configured to couple said spine to one of the plurality of biased struts.

2. The medical device as recited in claim 1, wherein said one or more branches comprise one or more first branches extending from a first side of said spine and one or more second branches extending from a second side of said spine.

3. The medical device as recited in claim 2, further comprising an actuating member, said actuating member engaging with said one or more first branches and said one or more second branches in an alternating manner as said actuating member engages with said one or more branches.

4. The medical device as recited in claim 1, wherein said mechanism substantially comprises NiTiNOL.

5. A medical device comprising:
    an elongate guide member comprising a lumen extending therethrough;
    an expandable filter coupled to the guide member;
    a securement mechanism comprising a spine having a first side and a second side, one or more branches extending from the first side and one or more branches extending from the second side, the securement mechanism mounted to the expandable filter; and
    an actuating member extending through the lumen and interacting with the securement mechanism such that the securement mechanism constrains the expandable filter when the actuating member is interacting with the securement mechanism;
    wherein the expandable filter has a proximal portion and a distal portion, and the securement mechanism constrains the proximal portion of the expandable filter;
    further comprising a sleeve adapted to constrain the distal portion of the expandable filter.

6. The medical device as recited in claim 5, wherein the sleeve is attached to the expandable filter.

7. The medical device as recited in claim 5, wherein the actuating member is stitched through the sleeve such that the sleeve constrains the distal portion of the expandable filter.

8. The medical device as recited in claim 7, wherein withdrawing the actuating member permits the securement mechanism and the sleeve to no longer constrain the expandable filter.

9. A medical device comprising:
    an elongate guide member comprising a lumen extending therethrough;
    an expandable filter coupled to the guide member;
    a securement mechanism comprising a spine having a first side and a second side, one or more branches extending from the first side and one or more branches extending from the second side, the securement mechanism mounted to the expandable filter; and
    an actuating member extending through the lumen and interacting with the securement mechanism such that the securement mechanism constrains the expandable filter when the actuating member is interacting with the securement mechanism;
    wherein the expandable filter comprises a biased strut, and the spine of the securement member is configured to be mounted to the biased strut;
    wherein the spine comprises a first aperture at a first end thereof and a second aperture at a second end thereof, where the biased strut passes through the first aperture and the second aperture in order to mount the securement member to the expandable filter.

* * * * *